United States Patent [19]

Barnett et al.

[11] 4,110,330
[45] Aug. 29, 1978

[54] 5'-ACETONYLVINCRISTINE AND RELATED COMPOUNDS

[75] Inventors: Charles J. Barnett; Richard A. Bimm, both of Indianapolis; George C. Cullinan, Trafalgar, all of Ind.

[73] Assignee: Eli Lilly and Company, Indianapolis, Ind.

[21] Appl. No.: 801,132

[22] Filed: May 27, 1977

[51] Int. Cl.$^2$ .......................................... C07D 519/04
[52] U.S. Cl. .................................................. 260/287 B
[58] Field of Search ..................................... 260/287 B

[56] References Cited

U.S. PATENT DOCUMENTS

| 3,097,137 | 7/1963 | Beer et al. | 260/287 B |
| 3,205,220 | 9/1965 | Svoboda et al. | 260/287 B |
| 3,370,057 | 4/1964 | Svoboda et al. | 260/287 B |
| 3,887,565 | 6/1975 | Jones et al. | 260/287 B |
| 3,890,325 | 6/1975 | Smith et al. | 260/287 B |
| 3,899,493 | 6/1975 | Jovanovics et al. | 260/287 B |
| 3,944,554 | 3/1976 | Tafur | 260/287 B |
| 3,954,773 | 5/1976 | Neuss et al. | 260/287 B |

Primary Examiner—Donald G. Daus
Assistant Examiner—David E. Wheeler
Attorney, Agent, or Firm—James L. Rowe; Arthur R. Whale

[57] ABSTRACT

5'-Acetonylvincristine and related compounds including the corresponding 1-desmethyl derivative, useful in inhibiting the growth of experimental tumors.

7 Claims, No Drawings

5'-ACETONYLVINCRISTINE AND RELATED COMPOUNDS

BACKGROUND OF THE INVENTION

Several naturally-occurring alkaloids obtainable from *Vinca rosea* have been found active in the treatment of experimental maliganancies in animals. Among these are leurosine (U.S. Pat. No. 3,370,057), vincaleukoblastine (vinblastine) to be referred to hereinafter as VLB (U.S. Pat. No. 3,097,137), leurosidine (vinrosidine) and leurocristine (VCR or vincristine) both in U.S. Pat. No. 3,205,220), deoxy VLB "A" and "B", *Tetrahedron Letters*, 783 (1968) (desacetyl leurosine hydrazide is also disclosed therein); 4-desacetoxyvinblastine (U.S. Pat. No. 3,954,773); 4-desacetoxy-3'-hydroxyvinblastine (U.S. Pat. No. 3,944,554); leurocolombine (U.S. Pat. No. 3,890,325), leuroformine (N-formylleurosine, see Belgian Pat. No. 811,110) and vincadioline (U.S. Pat. No. 3,887,565). Two of these alkaloids, VLB and leurocristine, are now marketed as drugs for the treatment of malignancies in humans, particularly the leukemias and related diseases.

The dimeric indoledihydroindole alkaloids obtainable from *Vinca rosea* can be represented by the formula:

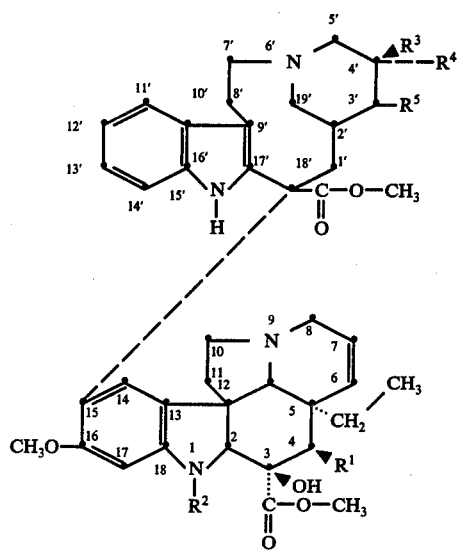

In the above formula where $R^1$ is acetoxy, $R^2$ is methyl, $R^3$ is hydroxyl, $R^4$ is ethyl and $R^5$ is H, VLB is represented; where $R^1$ is acetoxy, $R^2$ is formyl, $R^3$ is hydroxyl, $R^4$ is ethyl and $R^5$ is H, vincristine is represented; where $R^1$ is acetoxy, $R^2$ is methyl, $R^3$ is ethyl, $R^4$ is hyroxyl and $R^5$ is H, leurosidine is represented; where $R^1$ is acetoxy, $R^2$ is methyl, $R^3$ and $R^5$ are H and $R^4$ is ethyl, deoxy VLB "A" is represented; where $R^1$, $R^2$ and $R^5$ are the same as in deoxy VLB "A" but $R^3$ is ethyl and $R^4$ is hydrogen, deoxy VLB "B" is represented; and where $R^1$ is acetoxy, $R^2$ is methyl, $R^3$ is ethyl and $R^4$ and $R^5$ taken together form an α-epoxide ring, leurosine is represented.

Of the above alkaloids, vincristine is the most useful, and the least available, from Vinca. Recently, Jovanovics et al., U.S. Pat. No. 3,899,493, have developed a method for converting the relatively more abundant alkaloid VLB into vincristine in 50% or better yields by chromic acid oxidation at low (−60° C.) temperatures.

Derivatives of vincristine substituted at C-5' are not recorded in the literature.

SUMMARY OF THE INVENTION

This invention provides compounds represented by the following formulas:

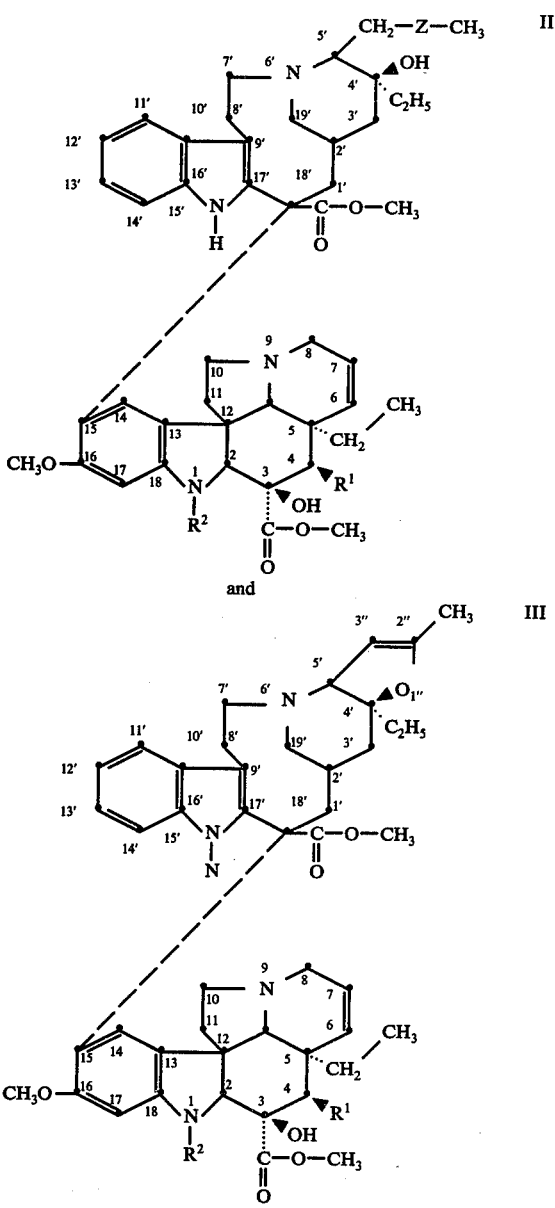

wherein Z is CO or CHOH, $R^2$ is H or CHO and $R^1$ is OH or acetoxy. The pharmaceutically-acceptable salts of the above bases formed with non-toxic acids are also included within the scope of this invention.

Compounds according to formula II wherein $R^2$ is CHO and H are named systematically as 5'-acetonylvincristine or 4-desacetyl-5'-acetonylvincristine and 5'-acetonyl-1-desformylvincristine or 4-desacetyl-1-desmethyl-5'-acetonylvincristine respectively. Compounds according to formula III are dehydration products of the 1",2"-hemiketals formed between the 5'-acetonyl carbonyl group and the 4'β-hydroxy group followed by 2",3" dehydration.

It is believed that the 5'-acetonyl derivatives (IV) are in dynamic equilibrium with the 1",2"-hemiketal derivatives (V) as shown in the following part formulas:

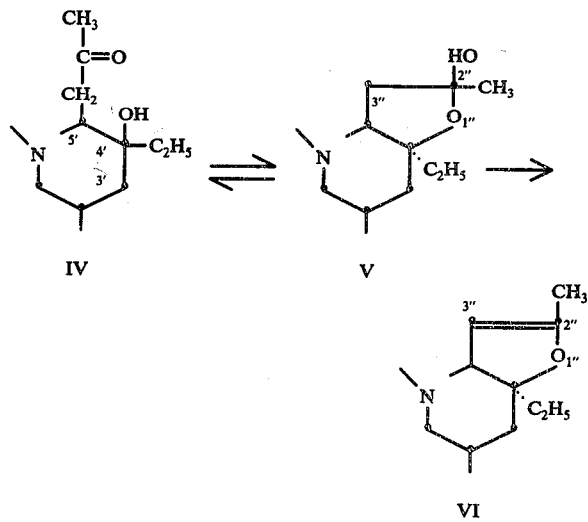

VI

The hemiketal (V), however, undergoes irreversible dehydration in the presence of a protic catalyst as for example an acid chalcide such as alumina, silica and the like. Thus attempts to chromatograph 5'-acetonylvincristine results in the production of two substances, purified 5'-acetonylvincristine and the corresponding dehydrated hemiketal produced from the 5'-acetonyl derivative by the action of the chromatographic medium in accordance with the equation IV ⇌ V → VI set forth above.

The compounds of this invention of formula II where Z is CO, $R^2$ is CHO and $R^1$ is acetoxy, are formed during a low temperature chromic acid oxidation of VLB in the presence of acetone. Reduction of the carbonyl in the 5'-acetonyl side chain as by diborane or other suitable selective metal hydride reducing agent, yields a compound in which Z is CHOH. Ordinarily, this reaction is carried out on 1-desformyl-4-desacetyl-5'-acetonylvincristine (prepared by the action of methanolic hydrochloric acid on 5'-acetonylvincristine) since the reducing agent also can react with the 1-formyl group and the 4-acetoxy group. The reduced 1-desformyl-4-desacetyl compound can readily be reformylated to yield a compound in which $R^2$ is CHO, Z is CHOH and R' is OH. Reactylation of C-4 can be carried out by the method of Hargrove, *Lloydia*, 27, 340 (1964) or by carefully controlled acetylation.

The compounds of this invention of formula III form more or less spontaneously by the dehydration of the 1",2"-hemiketal compound in equilibrium with the 5'-acetonyl derivative. Compounds according to formula III where $R^2$ is H and R' is OH or where $R^2$ is CHO and $R^1$ is acetoxy are prepared in similar fashion to the corresponding compounds of formula II.

Non-toxic acids useful for forming pharmaceutically-acceptable acid addition salts of the compounds of this invention include salts derived from inorganic acids such as: hydrochloric acid, nitric acid, phosphoric acid, sulfuric acid, hydrobromic acid, hydriodic acid, nitrous acid, phosphorous acid and the like, as well as salts of non-toxic organic acids including aliphatic mono and dicarboxylic acids, phenyl-substituted alkanoic acids hydroxy alkanoic and alkandioic acids, aromatic acids aliphatic and aromatic sulfonic acids, etc. Such pharmaceutically-acceptable salts thus include the sulfate pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, benzoate, chlorobenzoate, methylbenzoate, dinitrobenzoate, hydroxybenzoate methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, 2-hydroxybutyrate, glycollate, malate, tartrate, methanesulfonate, propanesulfonate, naphthalene-1-sulfonate, naphthalene-2-sulfonate and the like salts.

The compounds of this invention, represented by formulas II and III above, are synthesized as follows:

EXAMPLE 1

Preparation of 5'-Acetonylvincristine and the corresponding 1",2"-hemiketal

A solution was prepared from 50 g. of VLB sulfate and 6250 ml. of acetone. The solution was stirred and cooled to a temperature in the range of −65° C. to −70° C. A second solution containing 50 g. of chromium trioxide was prepared in 500 ml. of glacial acetic acid and 25 ml. of deionized water. This oxidizing solution was added to the solution of VLB in acetone over a 15 minute period with stirring while maintaining the temperature below about −50° C. The reaction was then quenched by adding it to a solution of 1900 ml. of deionized water containing 600 ml. of 14N aqueous ammonium hydroxide. The resulting pH should have been in the range 7.5–8.0 and if not, the pH was adjusted to a pH in that range by the addition of either 14N aqueous ammonium hydroxide or glacial acetic acid. The aqueous mixture was filtered and then concentrated under vacuum at a temperature below about 50° C. to remove acetone. The resulting aqueous mixture was extracted twice with equal volumes of methylene chloride. The methylene chloride extracts were combined, dried, and the methylene chloride removed therefrom by evaporation in vacuo, leaving as a residue a mixture of vincristine and 5'-acetonylvincristine among other products.

The residue from two VLB oxidations carried out as above (containing from 80 to 95G. weight) were dissolved in methylene chloride, the methylene chloride solution was filtered and the filtrate applied to a high pressure liquid chromatography column packed with Woelm activity III–IV alumina. The chromatogram was developed with a solvent mixture containing 25 parts ethyl acetate, 75 parts methylene chloride and 0.38 parts deionized water. Between 100–110 l. of eluant were required to elute substantially all material absorbed on the alumina. 5'-Acetonylvincristine and the corresponding dehydrated hemiketal (III where R is CHO) were eluted after fractions pure vincristine had been eluted. Fractions containing the two compounds were pooled, the solvent removed by evaporation in vacuo, the residue dissolved in chloroform, and the chloroform solution filtered and dried. Evaporation of the chloroform yielded a residue which was crystallized from methanol. The crystals were separated and the mother liquor concentrated to dryness in vacuo. The filtered crystals were predominantly vincristine, but the mother liquor contained substantial quantities of 5'-acetonylvincristine and the corresponding dehydrated-1'',2'''-hemiketal. Rechromatography of this residue (from the mother liquor) using preparative thin layer plate chromatography over alumina employing the same eluant as above, yielded purified 5'-acetonylvincristine and the corresponding dehydrated 1'',2'''-hemiketal also in pure form. The products were obtained as bands on the thin layer plates. The bands were separated mechanically and the purified compounds eluted therefrom with methanol.

The combined products had the following physical characteristics: molecular spectrum: peaks at 880 ($C_{49}H_{60}N_4O_{11}$) 862 ($C_{49}H_{58}N_4O_{10}$) 805 ($C_{46}H_{53}N_4O_9$), 484, 379, 192, 135, 122, 121.

Infrared absorption: peaks for free bases at 3460 (NH), 1740 (COO—) and 1685 (CON) $cm^{-1}$; sulfate salts at 1740 and 1680 $cm^{-1}$ NMR: δ at 3.64, 3.73, 8.75, 3.87, 2.07, 5.41, 5.90, 2.04 (new band indicating C—$CH_3$).

Ultra violet spectrum: λ at 210, 223, 255 and 297 mu.
Titration: pKa at 5.9 and 4.1.

5'-Acetonylvincristine had the following physical characteristics:

Mass spectrum: m/e = 880 (m) and 862 (m−18): high resolution = 880.42236

Empirical formula: $C_{49}H_{60}N_9O_{11}$ (error + 3.5 mmµ)

NMR: similar to vincristine except new peak at 2.04δ (3H singlet)

Infrared spectrum: absorption peaks at 3460 $cm^{-1}$ (NH), 1735 $cm^{-1}$ (C=O), 1680 $cm^{-1}$ (CON).

2'',3''-dehydro-5'-acetonylvincristine 1'',2'''-hemiketal had the following physical characteristics:

Mass spectrum: m/e = 862 (no 880 mass unit present)
NMR: similar to vincristine except new peak at 5.12δ (3'' hydrogen)

Infrared spectrum: absorption peaks at 3440 $cm^{-1}$ (NH), 1735 $cm^{-1}$ (C=O), 1680 $cm^{-1}$ (CON).

EXAMPLE 2

Preparation of
5'-acetonyl-1-desformyl-4-desacetylvincristine

Two grams of 5'-acetonylvincristine were dissolved in about 200 ml. of methanol saturated with gaseous hydrogen chloride at about 0° C. The solution was maintained at ambient temperature overnight. The volatile constituents were removed in vacuo and the residue containing 5'-acetonyl-1-desformyl-4-desacetylvincristine (as the hydrochloride salt) formed in the above reaction was dissolved in water. The resulting acidic solution was made basic with 14N aqueous ammonium hydroxide. 5'-acetonyl-1-desformyl-4-desacetylvincristine, being insoluble in the alkaline layer separated and was extracted into methylene chloride. The methylene chloride solution was dried and the methylene chloride removed by evaporation in vacuo. 5'-acetonyl-1-desformyl-4-desacetylvincristine remaining as a residue had the following physical characteristics:

Infrared spectrum: peak at 1720 $cm^{-1}$ (carboxyl); no peak for N—CHO group.

Molecular spectrum: m/e 792 (M−18), 413

The NMR spectrum was consistent with the proposed structure.

EXAMPLE 3

Preparation of 5'-Acetonyl-4-desacetylvincristine 500 mg. of 5'-Acetonyl-4-desformyl-4-desacetylvincristine were dissolved in a mixture of 24 ml. of 97 percent formic acid and 4 ml. of acetic anhydride. The reaction mixture was stirred at ambient temperatures for 2 hours after which time the volatile constituents were removed by evaporation. The residue was dissolved in methanol and the resulting solution again evaporated to dryness. This new residue was partitioned between methylene dichloride and water. The methylene dichloride layer was separated, washed with water, and the solvent removed by evaporation. The resulting residue comprising 5'-acetonyl-4-desacetylvincristine formed in the above reaction was purified by chromatography over silica gel using ethyl acetate methanol as the eluant. Fractions shown by TLC to contain 5'-acetonyl-4-desacetylvincristine were combined. 5'-Acetonyl-4-desacetylvincristine thus purified had the following physical characteristics:

Molecular spectrum: m/e 820 (Molecular ion − 18);
Infrared spectrum: new band at 1670 $cm^{-1}$ (amide carbonyl).

The NMR spectrum was consistent with the proposed structure.

The sulfate salt was prepared by adding 2 percent ethanolic sulfuric acid to an ethanol solution of the free base to pH = 4.1 and then evaporating the reaction mixture to dryness.

EXAMPLE 4

Preparation of
5'-(2''-hydroxypropyl)-1-desformyl-4-desacetylvincristine

A solution was prepared from 400 mg. of 5'-acetonyl-1-desformyl-4-desacetyl vincristine in 50 ml. of absolute ethanol at 0° C. 400 mg. of 96 percent sodium borohydride were added. The reaction mixture was stirred at about 0° C. for about 2 hours and was then quenched with 1N aqueous hydrochloric acid and water. The acidic mixture was made basic with 14N aqueous ammonium hydroxide. The aqueous alkaline layer was extracted twice with methylene chloride, the methylene chloride extracts were combined, and the combined extracts dried. Evaporation of the solvent from the dried combined extracts yielded compound of 5'-(2''-hydroxypropyl)-1-desformyl-4-desacetylvincristine formed in the above reaction. The residue was chromatographed over silica gel column using the 3:1 ethyl acetate-ethanol solvent mixture as the eluant. Fractions shown to contain 5'-(2''-hydroxypropyl)-1-desformyl-4-desacetylvincristine by thin-layer chromatography were combined. Evaporation of the solvent yielded 5'-(2''-hydroxypropyl)-1-desformyl-4-desacetylvincristine having the following physical characteristics:

Molecular spectrum: m/e = 812 (consistent with $C_{46}H_{60}N_4O_9$), 753, 413, 212.

EXAMPLE 5

Preparation of
5'-(2''-hydroxypropyl)-4-desacetylvincristine

Following the procedure of Example 3, 5'-(2''-hydroxypropyl)-1-desformyl-4-desacetylvincristine was formylated in a mixture of 3 ml. of acetic anhydride and 18 ml. of 97 percent formic acid. 5'-(2''-hydroxypropyl)-4-desacetylvincristine thus prepared was isolated by the procedure of Example 3. The compound was purified by chromatography over a preparative silica gel thin-layer plate using a 3:1 ethyl acetate-ethanol solvent mixture as eluant. 5'-(2''-hydroxypropyl)-4-desacetylvincristine thus purified had the following physical characteristics:

Infrared spectrum: peaks at 1715 and 1670 cm$^{-1}$.

EXAMPLE 6

Preparation of Salts

Sulfate salts of the free bases of this invention are prepared by dissolving the base in anhydrous ethanol and adjusting the pH of the resulting solution to about 4.25 with 2 percent ethanolic sulfuric acid. The resulting sulfate salt was isolated by evaporation in vacuo. These sulfate salts are water soluble tan amorphous powders. Other salts can be prepared by adding an equivalent of the acid in ethanol to an ethanolic solution of the base and then evaporating the solvents to leave the salt as a residue.

In each of the above examples, the acetonyl substitution product has been assigned to 5'-carbon as being the most probable site. This structure assignment has been based upon NMR considerations and on the interaction of the carbonyl group in the acetonyl side-chain with the 4'-hydroxyl on the ring. It should be recognized, however, that the assignment of structure is not yet based upon an unequivocal method of proof and that the acetonyl substituent could be present at other positions in the molecule, for example, at the 19'-carbon, a carbon also α to the nitrogen. It is intended herein to claim the acetonyl derivative of vincristine produced during the chromic acid oxidation at low temperature of vinblastine when carried out in the presence of acetone as set forth above.

The compounds of this invention are antimitotic agents being active in tissue culture and against transplanted tumors in mice. In demonstrating such activity against transplanted tumors in mice, a protocol was used which involved the administration of the drug, usually by the intraperitoneal route, at a given dose level for 3–10 days after innoculation with the tumor.

The following table — Table 1 — gives the results of several experiments in which mice bearing transplanted tumors were treated successfully with a compound of this invention. The following abbreviations are employed: Compound A is 5'-acetonylvincristine sulfate; B and C are the corresponding dehydrated hemiketal sulfate and free base; D is 4-desacetyl-5'-acetonylvincristine; GLS is Gardner lymphosarcoma; ROS is Ridgeway Osteogenic Sarcoma and CA755 is an adenocarcinoma. In the table, column 1 gives the compound designation; column 2, the abbreviation of the name of transplanted tumor; column 3, the dose level and the number of days that dosage was administered; and column 4, the percent inhibition of tumor growth or percent prolongation of survival time

| Compound | Tumor | Dose mg/kg × Days | Inhibition |
|---|---|---|---|
| A | CA755 | 0.3 × 8 | 21* |
|   |   | 0.5 × 8 | 39 |
|   |   | 0 × 8 | 39 |
|   |   | 5.0 × 8 | 34 |
| A | GLS | 0.05 × 9 | 8* |
|   |   | 0.1 × 7–9 | 6*, 25* |
|   |   | 0.2 × 7–9 | 2*, 20* |
|   |   | 0.3 × 7–9 | 13*, 39 |
|   |   | 0.5 × 7–9 | 49, 65 |
|   |   | 1.0 × 7–9 | 81, 86 |
| A | ROS | 0.05 × 10 | TOXIC |
|   |   | 0.1 × 10 | 0 |
|   |   | 0.2 × 10 | 60 |
|   |   | 0.3 × 10 | 34 |
|   |   | 0.5 × 10 | TOXIC |
|   |   | 1.0 × 10 | TOXIC |

-continued

| Compound | Tumor | Dose mg/kg × Days | Inhibition |
|---|---|---|---|
| C | GLS | 0.3 × 7 | 4*, 11* |
|   |   | 0.5 × 7 | 2*, 57 |
|   |   | 1.0 × 7 | 5*, 100 |
|   |   | 5.0 × 7 | 100, 100 |
| B | GLS | 0.1 × 7 | 0 |
|   |   | 0.2 × 7 | 21* |
|   |   | 0.3 × 7 | 22*, 37* |
|   |   | 0.5 × 7 | 54, 39, 59 |
|   |   | 1.0 × 7 | 100, 76, 96 |
|   |   | 5.0 × 7 | 100, 100 |
| B | GLS | 0.05 × 9 | 13* |
|   |   | 0.1 × 9 | 21* |
|   |   | 0.2 × 9 | 8* |
|   |   | 0.3 × 9 | 36 |
|   |   | 0.5 × 9 | 71 |
|   |   | 1.0 × 9 | 93 |
| B | ROS | 0.1 × 10 | 39 |
|   |   | 0.2 × 10 | 26 |
|   |   | 0.3 × 10 | 14* |
|   |   | 0.5 × 10 | 0* |
|   |   | 1.0 × 10 | 0* |
| A & B | GLS | 0.1 × 7 | 100 |
|   |   | 0.2 × 7 | 100 |
|   |   | 0.3 × 7 | 100 |
|   |   | 0.0125 × 10 | 0* |
|   |   | 0.5 × 10 | 0* |
|   |   | 0.2 × 10 | 13* |
|   |   | 0.5 × 10 | 83 |
|   |   | 1.0 × 10 | 100 |
| D | GLS | 0.3 × 7 | 0*, 0* |
|   |   | 0.5 × 7 | 37, 26 |
|   |   | 1.0 × 7 | 100, 62 |

*Activity not statistically significantly different from control.

The mixture of 5'-acetonylvincristine and of the corresponding 1",2"-dehydrated hemiketal is less toxic acutely than vincristine, showing only a 20 percent mortality at a 10 mg/kg. dose level. The LD$_{50}$ is greater than 10 mg./kg.

In utilizing the novel compounds of this invention separately or in mixtures as anti-tumor agents in mammals, the parenteral route of administration is conveniently employed. With parenteral administration, the intravenous route is preferred although with smaller mammals such as mice the intraperitoneal route may be used. For parenteral administration, isotonic solutions are employed containing 1–10 mg./ml. of a salt of the alkaloidal base (formula II or III or both). The compounds are administered at a rate of from 0.01 to 1 mg./kg. and preferably from 0.1 to 1 mg./kg. of mammalian body weight once or twice a week or every 2 weeks depending on both the activity and the toxicity of the drug. An alternative method of arriving at a therapeutic dose is based on body-surface area with a dose in the range 0.1 to 10 mg./meter squared of mammalian body surface every 7 or 14 days.

In utilizing a compound or mixture of compounds of this invention clinically as a drug, the clinical physician would administer the drug initially by the same route and in the same vehicle and probably against the same types of tumors as are indicated for vincristine or VLB. The dose levels employed would reflect the difference in dose levels found in the treatment of experimental tumors in mice. In clinical tests, as with other anti-tumor agents, particular attention would be paid to the effect of the oncolytic compounds of this invention against the 10 "signal" tumors set forth at page 266 of "The Design of Clinical Trials in Cancer Therapy" edited by Staquet (Futura Publishing Company, 1973).

We claim:

1. Compounds of the formula

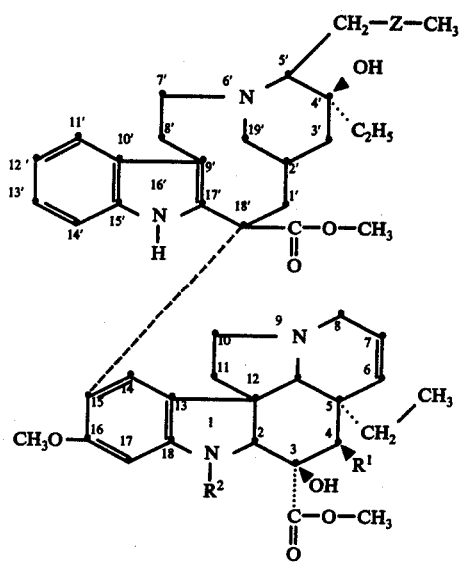

wherein Z is CO or CHOH, $R^2$ is H or CHO and $R^1$ is OH or acetoxy and pharmaceutically-acceptable salts thereof.

2. A compound according to claim 1, said compound being 5'-acetonylvincristine.

3. A compound according to claim 1, said compound being 4-desacetyl-5'-acetonylvincristine.

4. A compound according to claim 1, said compound being 1-desformyl-4-desacetyl-5'-acetonylvincristine.

5. A sulfate salt of a compound according to claim 1.

6. A compound according to claim 1, said compound being 5'-(2''-hydroxypropyl)-4-desacetylvincristine.

7. A compound according to claim 1, said compound being 5'-(2''-hydroxypropyl)-1-desformyl-4-desacetyl-vincristine.

* * * * *